United States Patent
Saito

(10) Patent No.: US 12,414,746 B2
(45) Date of Patent: Sep. 16, 2025

(54) RADIOGRAPHING APPARATUS

(71) Applicant: CANON KABUSHIKI KAISHA, Tokyo (JP)

(72) Inventor: Yohei Saito, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 253 days.

(21) Appl. No.: 18/048,771

(22) Filed: Oct. 21, 2022

(65) Prior Publication Data

US 2023/0125648 A1     Apr. 27, 2023

(30) Foreign Application Priority Data

Oct. 25, 2021  (JP) .................................. 2021-173697

(51) Int. Cl.
    *A61B 6/42*      (2024.01)
    *G01T 1/20*      (2006.01)
    *G01T 1/24*      (2006.01)

(52) U.S. Cl.
    CPC .......... *A61B 6/4283* (2013.01); *A61B 6/4233* (2013.01); *G01T 1/2006* (2013.01); *G01T 1/20189* (2020.05); *G01T 1/244* (2013.01)

(58) Field of Classification Search
    CPC ......... A61B 6/10; A61B 6/102; A61B 6/4233; A61B 6/4283; G01T 1/2006; G01T 1/20188; G01T 1/20189; G01T 1/244
    See application file for complete search history.

(56) References Cited

U.S. PATENT DOCUMENTS

| | | | |
|---|---|---|---|
| 6,972,410 B2 * | 12/2005 | Takeda .............. | H01L 27/14658 250/370.09 |
| 7,053,379 B2 * | 5/2006 | Watanabe .............. | G03B 42/02 250/370.11 |
| 7,397,037 B2 * | 7/2008 | Watanabe .............. | G03B 42/02 250/580 |
| 9,104,097 B2 * | 8/2015 | Suwa ................... | A61B 6/4283 |
| 9,980,687 B2 * | 5/2018 | Rieuvernet .......... | A61B 6/4405 |
| 10,024,980 B2 * | 7/2018 | Suzuki ................. | G01T 1/2006 |
| 10,045,748 B1 * | 8/2018 | Konkle .................... | G01T 1/244 |
| 10,274,613 B2 * | 4/2019 | Suzuki ................... | G01N 23/04 |
| 10,690,789 B2 * | 6/2020 | Horiuchi .............. | G01T 1/2006 |

(Continued)

FOREIGN PATENT DOCUMENTS

| | | | |
|---|---|---|---|
| FR | 3019907 A1 * | 10/2015 | .......... A61B 6/4216 |
| JP | 2019113403 A | 7/2019 | |

(Continued)

OTHER PUBLICATIONS

Machine translation of FR 3019907 A1 (Year: 2015).*
Machine translation of KR 101127122 B1 (Year: 2012).*

*Primary Examiner* — Thomas R Artman
(74) *Attorney, Agent, or Firm* — Canon U.S.A., Inc. IP Division

(57) ABSTRACT

An X-ray imaging apparatus includes a sensor panel that converts incident radiation to an electric signal, a tabular metallic base plate including a front surface where the sensor panel is supported and a region where the tabular metallic base plate has a basic thickness, a circuit board disposed on a rear surface of the tabular metallic base plate, the rear surface being opposite to the front surface, wherein a thickness of the tabular metallic base plate in a region where the circuit board is disposed is larger than the basic thickness.

9 Claims, 5 Drawing Sheets

(56) References Cited

U.S. PATENT DOCUMENTS

| | | | |
|---|---|---|---|
| 10,721,839 B2* | 7/2020 | Tagawa | G01T 1/244 |
| 10,732,308 B2* | 8/2020 | Noguchi | G01T 7/00 |
| 11,079,503 B2* | 8/2021 | Horiuchi | A61B 6/4283 |
| 11,099,286 B2* | 8/2021 | Horiuchi | G01T 1/2006 |
| 2003/0026382 A1* | 2/2003 | Takeda | H04N 23/30 |
| | | | 378/19 |
| 2004/0211909 A1* | 10/2004 | Watanabe | G03B 42/02 |
| | | | 250/370.11 |
| 2006/0157658 A1* | 7/2006 | Watanabe | G03B 42/02 |
| | | | 250/580 |
| 2012/0168632 A1* | 7/2012 | Yagi | G01T 1/20 |
| | | | 250/366 |
| 2012/0195409 A1* | 8/2012 | Suwa | G03B 42/04 |
| | | | 378/189 |
| 2015/0293237 A1* | 10/2015 | Suzuki | G03B 42/04 |
| | | | 250/369 |
| 2015/0320373 A1* | 11/2015 | Rieuvernet | A61B 6/4405 |
| | | | 378/189 |
| 2017/0090044 A1* | 3/2017 | Suzuki | A61B 6/4283 |
| 2018/0321392 A1* | 11/2018 | Suzuki | G01T 1/2006 |
| 2019/0110376 A1* | 4/2019 | Tagawa | H05K 7/20436 |
| 2019/0196033 A1* | 6/2019 | Horiuchi | G01T 1/244 |
| 2019/0196034 A1* | 6/2019 | Noguchi | G03B 42/02 |
| 2019/0196036 A1* | 6/2019 | Horiuchi | G01T 7/005 |
| 2020/0278462 A1* | 9/2020 | Horiuchi | G01T 7/005 |
| 2023/0011527 A1* | 1/2023 | Takeuchi | G01T 1/20 |
| 2023/0125648 A1* | 4/2023 | Saito | G01T 1/2006 |
| | | | 250/370.09 |

FOREIGN PATENT DOCUMENTS

| | | | | |
|---|---|---|---|---|
| KR | 101127122 B1 * | 3/2012 | | |
| WO | WO-2012165155 A1 * | 12/2012 | | G01T 1/2018 |

* cited by examiner

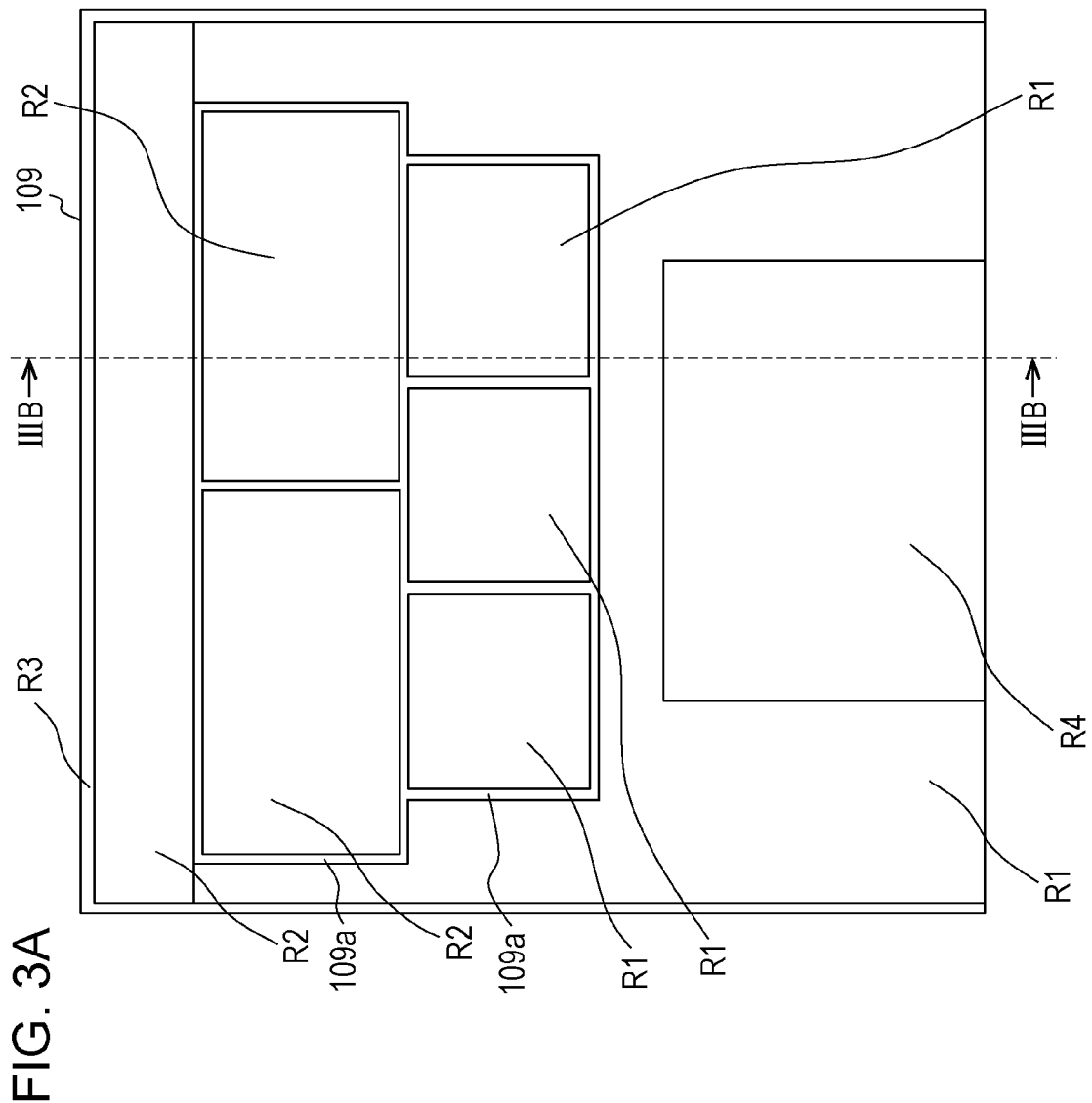

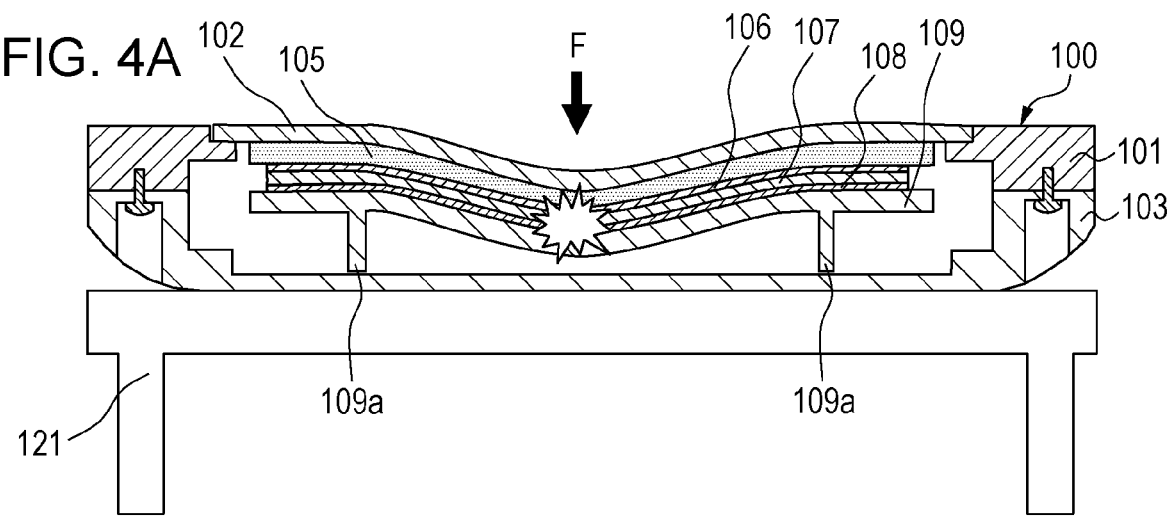
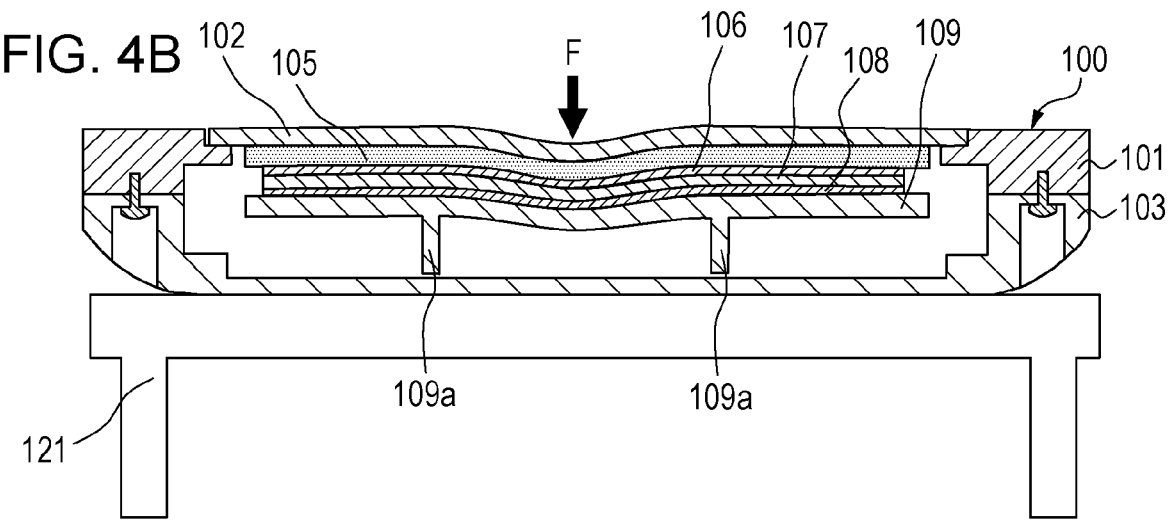
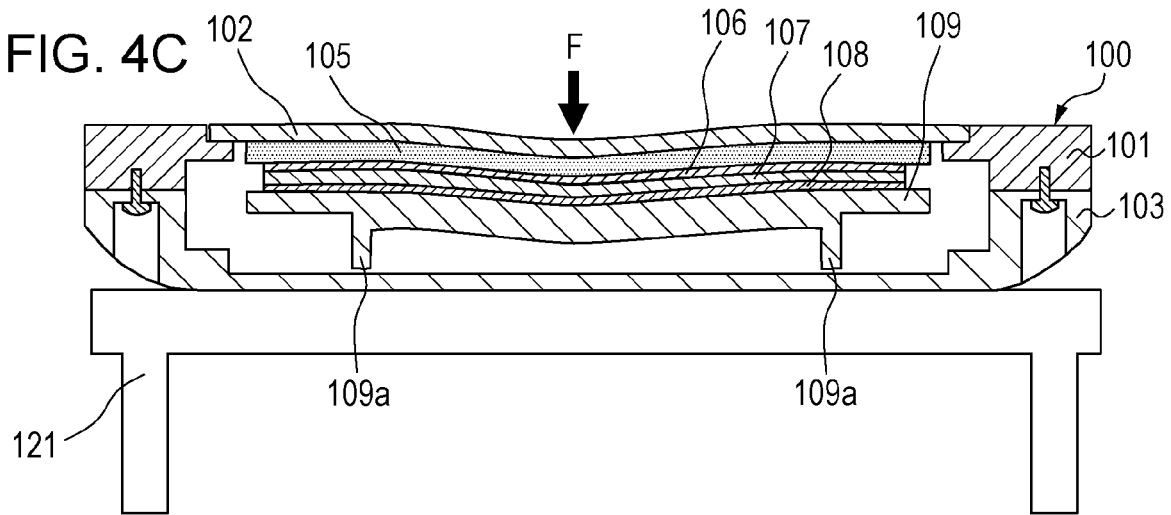

RADIOGRAPHING APPARATUS

BACKGROUND OF THE INVENTION

Field

The present disclosure relates to a radiographing apparatus to be applied, for example, to medical imaging systems.

Description of the Related Art

X-ray imaging apparatuses are widely used, for example, in the field of medicine. An X-ray imaging apparatus emits X-rays to a subject and forms an image based on the intensity distribution of the X-rays that have passed through the subject. A portable X-ray imaging apparatus is available, and such an X-ray imaging apparatus needs to be lightweight for the convenience of portability. The X-ray imaging apparatus is placed under a subject when in use and the weight of the subject is applied thereto during image capturing. Accordingly an increased strength is needed for the X-ray imaging apparatus. The increased strength is needed also because a user may drop the portable X-ray imaging apparatus. Accordingly, weight reduction and increased strength are needed for the portable X-ray imaging apparatus.

Japanese Patent Laid-Open No. 2019-113403 discloses an apparatus that includes a support member supporting a radiation detection panel, cylindrically shaped multiple first projections and a second projection. The first projections and the second projection are formed on a surface of the support member, the surface being opposite to a surface on which the radiation detection panel is supported. The second projection is shorter in length than the first projections in a direction normal to the surface on which the radiation detention panel is supported.

According to Japanese Patent Laid-Open No. 2019-113403, the thickness of the support member is uniform, and the first projections, which are in contact with the inside surface of a housing, are disposed uniformly. Accordingly, the strength is uniform over the entire apparatus. The apparatus having a uniform strength over the entire apparatus, however, does not necessarily lead to weight reduction because, for example, the projections are formed in a region in which the strength is not demanded. In other words, the apparatus cannot necessarily achieve an appropriate balance between weight reduction and increased strength.

SUMMARY

Accordingly, the present invention provides a radiographing apparatus that can achieve an appropriate balance between weight reduction and increased strength.

According to an aspect of the disclosure, a radiographing apparatus includes a sensor panel configured to convert incident radiation to an electric signal, a tabular metallic base plate including a front surface where the sensor panel is supported and a region where the tabular metallic base plate has a basic thickness, and a circuit board disposed on a rear surface of the tabular metallic base plate, the rear surface being opposite to the front surface, wherein, a thickness of the tabular metallic base plate in a region where the circuit board is disposed is larger than the basic thickness.

Further features of the present disclosure will become apparent from the following description of exemplary embodiments with reference to the attached drawings.

BRIEF DESCRIPTION OF THE DRAWINGS

FIGS. 3A and 3B are views illustrating a tabular metallic base plate of the X-ray imaging apparatus according to the embodiment.

FIGS. 4A, 4B, and 4C are views schematically illustrating the X-ray imaging apparatus when a load is applied to the X-ray imaging apparatus.

DESCRIPTION OF THE EMBODIMENTS

An embodiment of the present disclosure will be described with reference to the attached drawings.

In the present embodiment, a portable X-ray imaging apparatus, which is otherwise called an "electronic cassette", will be described as an example of a radiographing apparatus to which the present disclosure is applied.

Figure 1A:
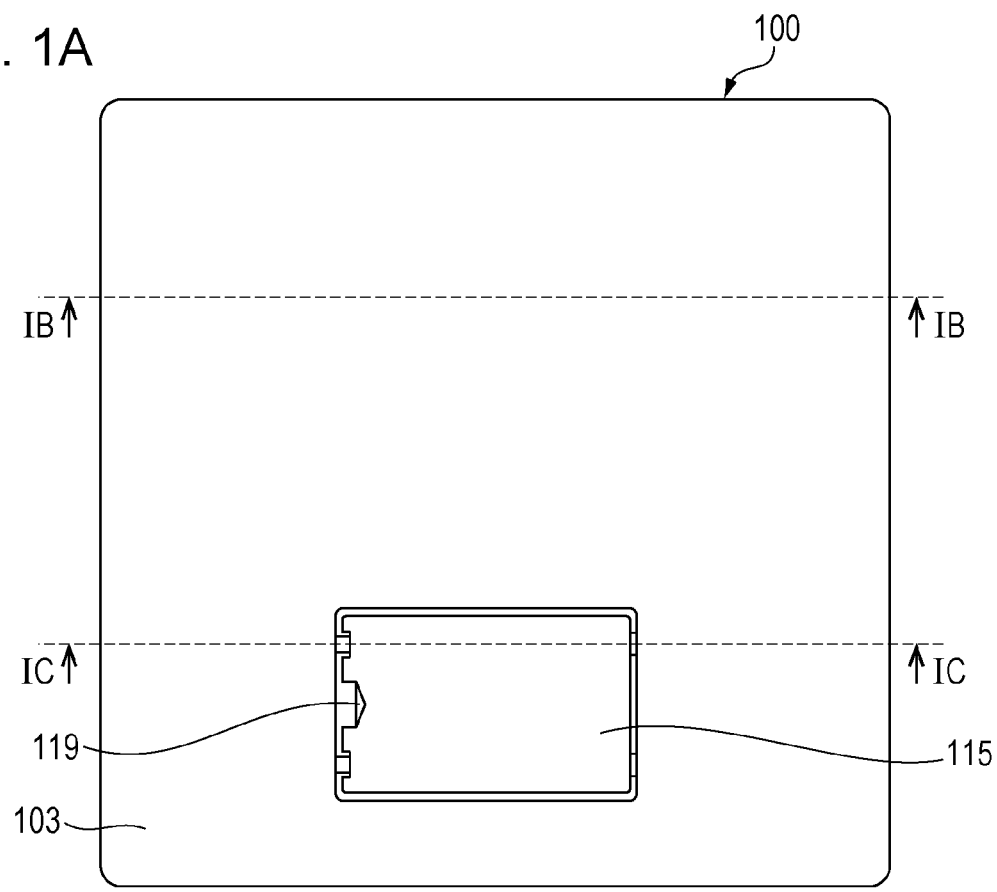
FIGS. 1A, 1B, and 1C are views illustrating an X-ray imaging apparatus according to an embodiment.
Figure 1B:
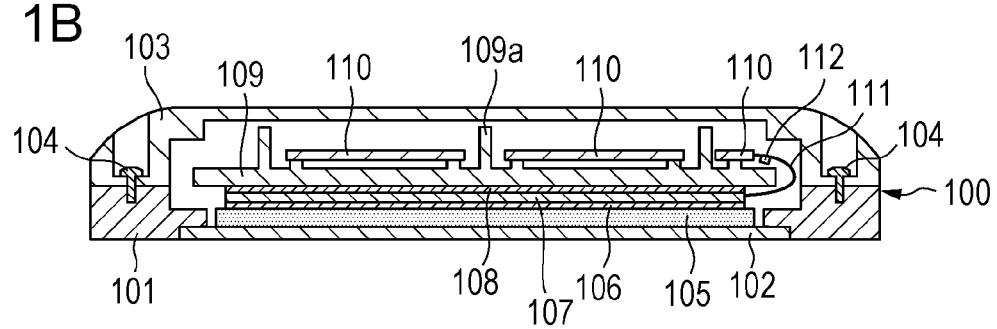
Figure 1C:
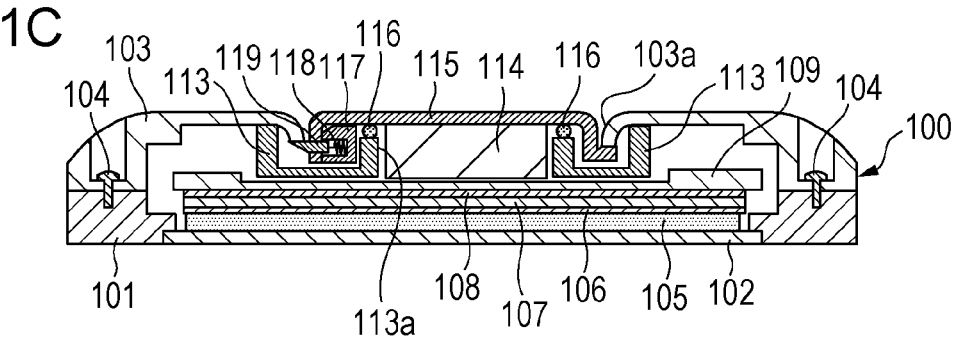

FIGS. 1A, 1B, and 1C are views illustrating the X-ray imaging apparatus according to the present embodiment, in which FIG. 1A is a rear view, FIG. 1B is a cross-sectional view taken along line IB-IB, and FIG. 1C is a cross-sectional view taken along line IC-IC. For description purposes, the up-down direction in FIG. 1A is referred to as a "longitudinal direction" of the X-ray imaging apparatus, and the right-left direction in FIG. 1A is referred to as a "transverse direction" of the X-ray imaging apparatus.

The X-ray imaging apparatus includes a flat and box-like housing 100 that covers the X-ray imaging apparatus. The housing 100 includes a front frame 101, an entrance face plate 102 attached to the front frame 101, and a rear housing segment 103.

The front frame 101 is made of, for example, a magnesium alloy or an aluminum alloy. X-rays are incident on the front surface of the entrance face plate 102. The entrance face plate 102 is made of, for example, a lightweight and high-rigidity material having a low X-ray absorption property, such as a carbon fiber reinforced plastic (CFRP). The rear housing segment 103 is made of, for example, a magnesium alloy or an aluminum alloy. The front frame 101 and the rear housing segment 103 are fixed to each other using fastening members 104, such as screws. A gasket (not illustrated) is provided between the front frame 101 and the rear housing segment 103, which makes the inside of the housing 100 a sealed space.

As illustrated in FIG. 1B, a shock absorbing member 105 for absorbing shocks is disposed on the entrance face plate 102 in the sealed space inside the housing 100. A fluorescent member 106 is disposed behind the shock absorbing member 105. The fluorescent member 106 is made of a fluorescent material, such as GOS or CsI, which scintillates in response to the incident X-rays that have passed through a subject. A sensor panel 107 is secured to the rear surface of the fluorescent member 106. The sensor panel 107 can store electric charges when the sensor panel 107 receives light emitted from the fluorescent member 106. The sensor panel 107 then converts the incident radiation into electric signals. A shield member 108 is disposed on the rear surface of the sensor panel 107 to reduce the impact of the X-rays that have passed through the sensor panel 107. A tabular metallic base plate 109 that is shaped substantially rectangularly is disposed on the rear surface of the shield member 108. The tabular metallic base plate 109 is made of, for example, a magnesium alloy or an aluminum alloy. The front surface of the tabular metallic base plate 109 supports the sensor panel 107 and other members. The fluorescent member 106, the sensor panel 107, the shield member 108, and the tabular metallic base plate 109 are secured to each other using, for example, a double-sided adhesive tape. The front frame 101, the rear housing segment 103, and the tabular metallic base plate 109 can be made of the same metal, such as a magnesium alloy.

Multiple electric circuit boards 110 are disposed on the rear surface of the tabular metallic base plate 109, the rear surface being opposite to the front surface. The rear surface of the tabular metallic base plate 109 supports the electric circuit boards 110. The electric circuit boards 110 receive the electric charges stored in the sensor panel 107 and thereby process images. The electric circuit boards 110 also control the X-ray imaging apparatus. Some of the electric circuit boards 110 are connected to the sensor panel 107 via flexible circuit boards 111 through which electric signals are transmitted from the sensor panel 107 to the electric circuit boards 110. The flexible circuit boards 111 have respective integrated circuits (ICs) 112 that amplify the electric signals from the sensor panel 107.

As illustrated in FIG. 1C, an opening 103a that is shaped substantially rectangularly is formed in the rear housing segment 103. A battery holding member 113 is secured to the inside surface of the rear housing segment 103 using, for example, an adhesive or a double-sided adhesive tape at a position corresponding to the opening 103a. A battery accommodation space 113a is formed through the battery holding member 113 to oppose the opening 103a. The battery accommodation space 113a is a rectangularly shaped through-hole, and a battery 114 is accommodated and secured therein.

A metallic cover 115, which is made of aluminum alloy or the like, is detachably attached to the rear housing segment 103 to cover the opening 103a. A gasket 116 is disposed between the inside surface of the cover 115 and the battery holding member 113 to surround the battery accommodation space 113a. The gasket 116 is, for example, secured to the inside surface of the cover 115 using an adhesive or a double-sided adhesive tape.

A locking member 117 is fixed to the inside surface of the cover 115 by a screw or the like (not illustrated). The locking member 117 includes an urging spring 118 and a latch 119. The urging force of the urging spring 118 causes the latch 119 to protrude sideways from the cover 115 and engage the edge of the opening 103a. When the cover 115 is installed, the urging force of the urging spring 118 causes the latch 119 to engage the edge of the opening 103a and to bring the cover 115 into a locked state in which the cover 115 is not detachable. In the locked state, the gasket 116 is pressed flat to maintain the sealing of the battery accommodation space 113a, which can, for example, prevent water from entering the accommodation space for the battery 114 when washing the apparatus. When the cover 115 is removed, the latch 119 is pressed in against the urging force of the urging spring 118, which unlocks and releases the cover 115 from the edge of the opening 103a.

Next, components disposed inside the X-ray imaging apparatus of the present embodiment will be described with reference to FIGS. 2A and 2B.

Figure 2A:
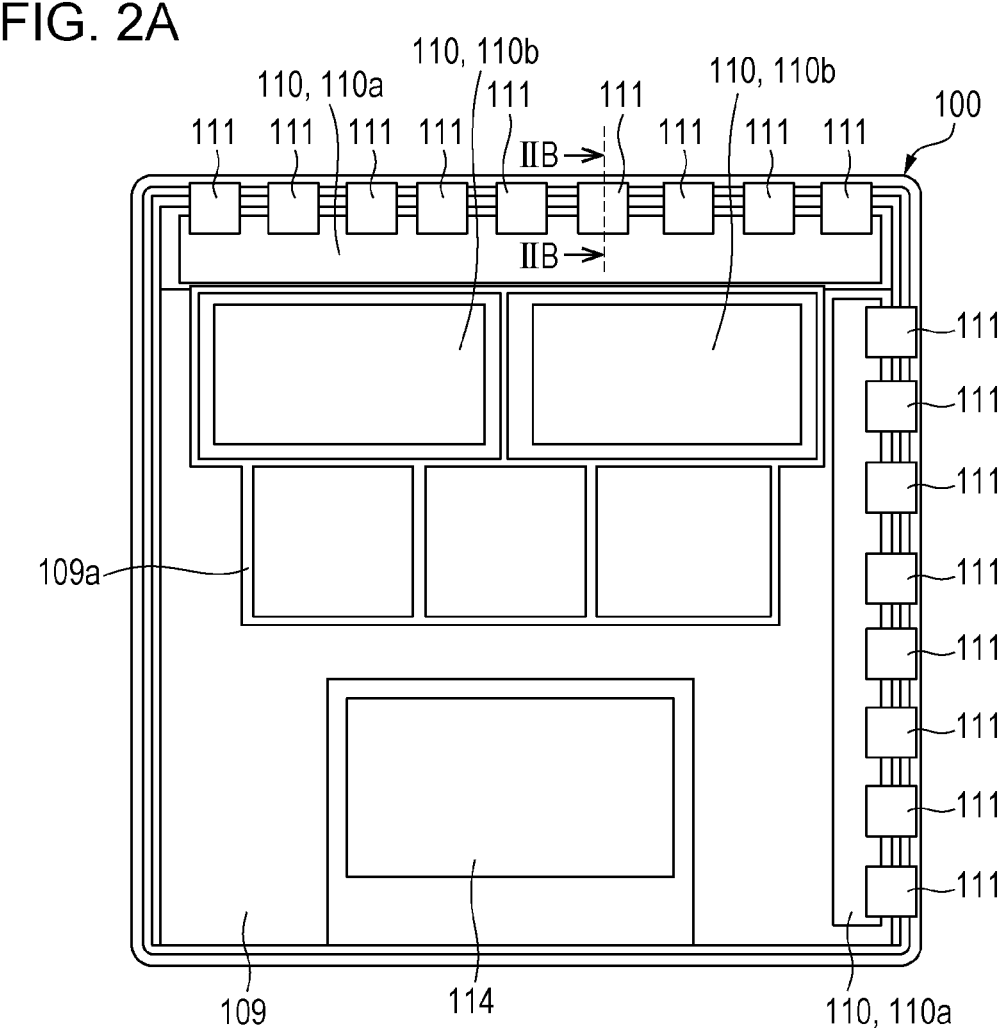
FIGS. 2A and 2B are views illustrating the X-ray imaging apparatus according to the embodiment.
Figure 2B:
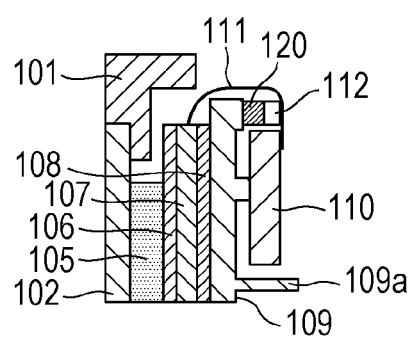

FIGS. 2A and 2B are views illustrating the X-ray imaging apparatus of the present embodiment, where FIG. 2A is a rear view when the rear housing segment 103 is removed and FIG. 2B is a cross-sectional view taken along line IIB-IIB in FIG. 2A.

As described above, the rear surface of the tabular metallic base plate 109 supports multiple electric circuit boards 110, with some of the electric circuit boards 110 connected to the sensor panel 107 via the flexible circuit boards 111.

The electric circuit boards 110 can have different shapes depending on their functions. For example, electric circuit boards 110a to be connected to the sensor panel 107 via the flexible circuit boards 111 are disposed along respective edges of the tabular metallic base plate 109. Each of the electric circuit boards 110a has an elongated rectangular shape with a length almost equal to the longitudinal length or the transverse length of the sensor panel 107. Electric circuit boards 110b process images and control the X-ray imaging apparatus and have many electric elements, which need to be arranged efficiently. Each of the electric circuit boards 110b has a rectangular shape with longer sides exceeding 100 mm, which is approximately twice as long as the short sides. In the present embodiment, two electric circuit boards 110b are disposed on one side of the rear surface of the X-ray imaging apparatus in the longitudinal direction of the X-ray imaging apparatus (i.e., on the upper side of the X-ray imaging apparatus in FIG. 2A). The two electric circuit boards 110b are arranged side by side in the transverse direction of the X-ray imaging apparatus.

The ICs 112, which are installed in respective flexible circuit boards 111, are readily affected by, for example, vibration. Accordingly, each IC 112 contacts the tabular metallic base plate 109 with an elastic member 120 interposed there between. The elastic member 120 is made of, for example, rubber.

The battery 114 is accommodated in the battery holding member 113 at a position different from where the electric circuit boards 110 are disposed. In other words, the battery 114 is disposed on the other side of the rear surface of the X-ray imaging apparatus in the longitudinal direction of the X-ray imaging apparatus (i.e., on the lower side of the X-ray imaging apparatus in FIG. 2A).

Next, the tabular metallic base plate 109 of the X-ray imaging apparatus according to the present embodiment will be described with reference to FIGS. 3A and 3B, FIGS. 4A to 4C, and FIGS. 5A and 5B.

FIGS. 3A and 3B are views illustrating the tabular metallic base plate 109 of the X-ray imaging apparatus of the present embodiment, where FIG. 3A is a rear view and FIG. 3B is a cross-sectional view taken along line IIIB-IIIB in FIG. 3A.

Ribs 109a are formed to protrude from the rear surface of the tabular metallic base plate 109. The ribs 109a serve as support portions that abut and support the inside surface of the rear housing segment 103 of the housing 100. In one exemplary embodiment, the ribs 109a can always be contact the inside surface of the housing 100. In another exemplary embodiment, the ribs 109a can oppose the inside surface of the housing 100 with gaps interposed there between. In this embodiment, the ribs 109a can contact the inside surface of the housing 100 when the tabular metallic base plate 109 deforms due to a load being applied thereto.

In the present embodiment, the ribs 109a are disposed to surround each of the two electric circuit boards 110b arranged side by side in the transverse direction of the X-ray imaging apparatus. The ribs 109a are also disposed to surround each of the three rectangular regions arranged side by side at a position under the two electric circuit boards 110b.

The rear surface of the tabular metallic base plate 109 are divided into a first region R1, a second region R2, a third region R3, and a fourth region R4 depending on members disposed therein. The first region R1 is a region where a member, such as an electric circuit board 110 or a battery 114, is not disposed. The first region R1 has a basic thickness t1. The second region R2 is a region where the electric circuit boards 110 are disposed. The third region R3 is a region where the ICs 112 installed in respective flexible circuit boards 111 are disposed. The fourth region R4 is a region where the battery holding member 113 is disposed. The battery 114, which serves as a power supply member, is accommodated and secured in the battery holding member 113.

The regions R1 to R4 will now be described in more detail.

The first region R1 is the region where a member, such as the electric circuit board 110 or the battery 114, is not disposed. The first region R1 has the basic thickness t1. The first region R1 is larger in area compared with the other regions R2 to R4. The first region R1 can be designed more flexibly because no member is disposed on the rear surface of the tabular metallic base plate 109, which enables the ribs 109a to be disposed more flexibly to decrease the distance between adjacent ribs 109a. In the present embodiment, the distance between adjacent ribs 109a is smaller in the first region R1 than in the second region R2.

The strength of the apparatus can be obtained by adjusting the thickness of the tabular metallic base plate 109 and by disposing the ribs 109a. This will be described in more detail with reference to FIGS. 4A to 4C. FIGS. 4A to 4C are views schematically illustrating a state where a load F is applied onto the X-ray imaging apparatus when the X-ray imaging apparatus is placed on a bed 121 with the front surface facing upward and a subject lies over the X-ray imaging apparatus.

FIGS. 4A and 4B illustrate examples where the distances between adjacent ribs 109a are large and small, while the thickness of the tabular metallic base plate 109 remains the same.

FIG. 4A is a comparative example in which the distance between adjacent ribs 109a of the tabular metallic base plate 109 is large. The same reference signs used for the X-ray imaging apparatus of the present embodiment are also used here for ease of description. The load F causes the entrance face plate 102 and the shock absorbing member 105 to deform. The deformation of the shock absorbing member 105 applies an additional load to the fluorescent member 106, the sensor panel 107, the shield member 108, and the tabular metallic base plate 109. In this case, the tabular metallic base plate 109 deforms between adjacent ribs 109a because of the large distance there between, which can lead to breakage of the sensor panel 107.

FIG. 4B is an example where the distance between adjacent ribs 109a of the tabular metallic base plate 109 is made small in the first region R1. The load F causes the entrance face plate 102 and the shock absorbing member 105 to deform. The deformation of the shock absorbing member 105 applies an additional load to the fluorescent member 106, the sensor panel 107, the shield member 108, and the tabular metallic base plate 109. In this case, the deformation of the tabular metallic base plate 109 can be suppressed between the ribs 109a where the distance is small. Even in the case of the thickness t1 being relatively small in the first region R1, the ribs 109a can be disposed flexibly to increase the rigidity in the first region R1 where a high rigidity is demanded. As a result, the balance between weight reduction and increased strength can be optimized for the X-ray imaging apparatus.

The second region R2 is a region where the electric circuit boards 110 are disposed. Due to the electric circuit boards 110 being disposed on the rear surface of the tabular metallic base plate 109, the design flexibility is limited in the second region R2. Because the distance between adjacent ribs 109a is large and the disposal of the ribs 109a is less flexible, the second region R2 is vulnerable to the breakage described in relation to FIG. 4A.

In the second region R2, the thickness t2 of the tabular metallic base plate 109 is made larger than the basic thickness t1 to obtain rigidity. FIG. 4C illustrates an example in which the distance between adjacent ribs 109a remains the same as that in FIG. 4A but the thickness of the tabular metallic base plate 109 is made larger compared with the examples in FIGS. 4A and 4B. The load F causes the entrance face plate 102 and the shock absorbing member 105 to deform. The deformation of the shock absorbing member 105 applies an additional load to the fluorescent member 106, the sensor panel 107, the shield member 108, and the tabular metallic base plate 109. In this case, the deformation of the tabular metallic base plate 109 can be suppressed between adjacent ribs 109a because the increased thickness of the tabular metallic base plate 109 increases the rigidity. Even in the case in which the distance between adjacent ribs 109a is large and the disposal of the ribs 109a is less flexible in the second region R2, the thickness of the tabular metallic base plate 109 can be increased to increase the rigidity in the second region R2 where a high rigidity is demanded. Accordingly, the balance between weight reduction and increased strength can be optimized for the X-ray imaging apparatus.

The area of the second region R2 can be set to be substantially equal to the area in which the electric circuit boards 110 are supported, and the ribs 109a can be disposed to surround each electric circuit board 110. Accordingly, a desired strength can be obtained with a minimum increase in the mass.

The thickness of the tabular metallic base plate 109 does not need to be uniform in the second region R2. The part having the thickness t2 can be formed in a grid-like manner in the second region R2.

The third region R3 is a region where the ICs 112 installed in the flexible circuit boards 111 are disposed. In other words, the third region R3 is a region that overlaps the ICs 112 as viewed in a direction normal to the rear surface of the tabular metallic base plate 109. The ICs 112 are small components, and accordingly, the area of the third region R3 is smaller than the area of the second region R2. The ICs 112 are electronic components that affect the image quality considerably even if they are small. The ICs 112 are vulnerable, for example, to vibrations, and the vibrations can cause noises in the image. Accordingly, as illustrated in FIG. 2B, each IC 112 contacts the tabular metallic base plate 109 with an elastic member 120, such as rubber, being interposed there between. The ICs 112 tend to receive external forces readily. Accordingly, the tabular metallic base plate 109 needs to have a strength. It is difficult, however, to provide the ribs 109a in this region because the flexible circuit boards 111 are present.

In order to obtain the rigidity in the third region R3, the thickness t3 of the tabular metallic base plate 109 is made larger than the thickness t2 in the second region R2. The thickness of the tabular metallic base plate 109 is increased discretely for the region where the components that cannot withstand a large load, such as the ICs 112, are disposed.

Accordingly, a required rigidity can be obtained, while the weight of the tabular metallic base plate 109 can be controlled.

In general, the ICs 112 tend to generate heat. The ICs 112 are mounted on the flexible circuit boards 111, which are typically thin and poor in thermal conductivity. Accordingly, the ICs 112 themselves can produce noises due to heat generation. Thus, a heat conductive rubber is used for the elastic member 120, which facilitates heat conduction to the tabular metallic base plate 109. An increase in the thickness t3 in the third region R3 improves heat conduction inside the tabular metallic base plate 109, which can reduce noise generation caused by the heat of the ICs 112.

In the present embodiment, the thickness t3 in the third region R3 is made larger than the thickness t2 in the second region R2. The thickness t3 in the third region R3, however, can be equal to the thickness t2 in the second region R2.

The fourth region R4 is a region where the battery holding member 113 is disposed. The battery holding member 113 accommodates and secures the battery 114. The battery 114 is armored by a resin cover that covers a storage unit and a circuit unit of the battery 114. The battery 114 itself can withstand a load. The battery 114 is secured so it contacts the tabular metallic base plate 109. More specifically, the battery 114 can always contact the tabular metallic base plate 109 or can contact the tabular metallic base plate 109 when the tabular metallic base plate 109 deforms. The gap between the tabular metallic base plate 109 and the battery 114 can be as small as possible.

The thickness t4 of the fourth region R4 is made smaller than the basic thickness t1.

Figure 5A:
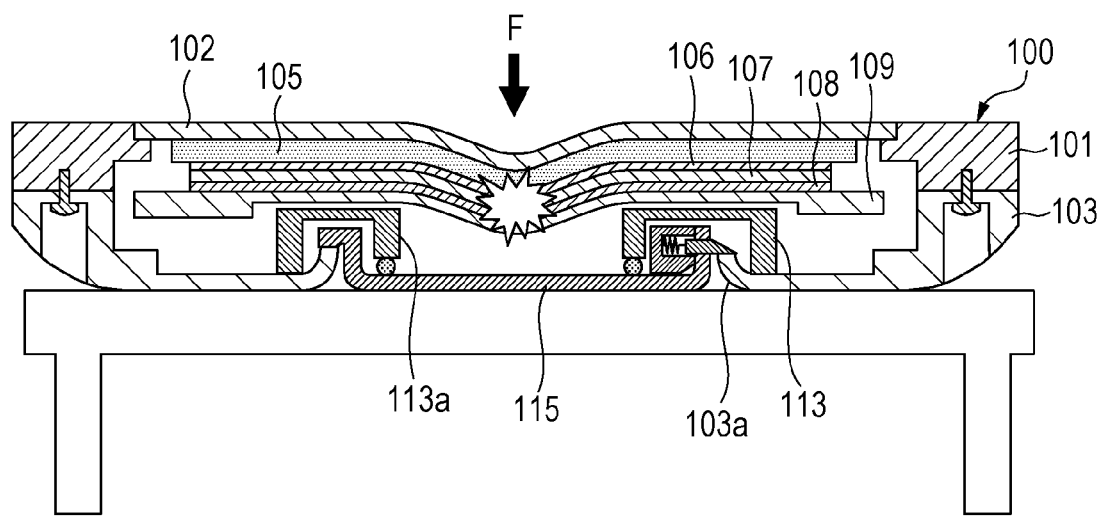
FIGS. 5A and 5B are other views schematically illustrating the X-ray imaging apparatus when a load is applied to the X-ray imaging apparatus.
Figure 5B:
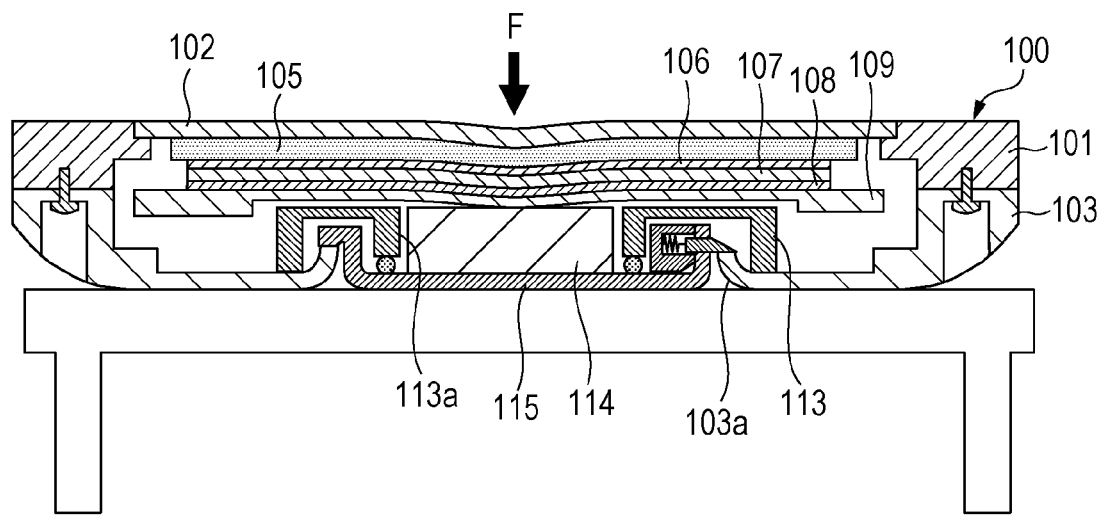

Referring to FIGS. 5A and 5B, the following describes how the X-ray imaging apparatus provides a sufficient durability in the fourth region R4 even if the thickness t4 in the fourth region R4 is reduced. FIGS. 5A and 5B are views schematically illustrating a state where a load F is applied onto the X-ray imaging apparatus when the X-ray imaging apparatus is placed on a bed 121 with the front surface facing upward and a subject lies over the X-ray imaging apparatus.

FIG. 5A illustrates a state where the load F is applied to the X-ray imaging apparatus while the battery 114 is not installed. FIG. 5B illustrates a state where the load F is applied to the X-ray imaging apparatus while the battery 114 is installed. The load F causes the entrance face plate 102 and the shock absorbing member 105 to deform. The deformation of the shock absorbing member 105 applies an additional load to the fluorescent member 106, the sensor panel 107, the shield member 108, and the tabular metallic base plate 109. In this case, if the battery 114 is not present as illustrated in FIG. 5A, the tabular metallic base plate 109 can deform at the battery accommodation space 113a. If the battery 114 is present as illustrated in FIG. 5B, the battery 114 and the tabular metallic base plate 109 areally contact each other, which prevents local deformation of the tabular metallic base plate 109 and thereby reduces the deformation of the tabular metallic base plate 109. The thickness t4 in the fourth region R4 can then be made smaller than the basic thickness t1, which can reduce the weight of the apparatus.

In general, the capacity of the battery 114 increases in proportion to the size thereof. The size of the battery 114 can increase as the thickness t4 in the fourth region R4 decreases, which advantageously leads to an increase in the capacity of the battery 114.

As described above, the rear surface of the tabular metallic base plate 109 are divided into multiple regions depending on members disposed therein, and the thicknesses and the disposal of the ribs 109a can be set appropriately in respective regions to obtain an appropriate balance between weight reduction and increased strength.

In the X-ray imaging apparatus of the present embodiment, as illustrated in FIG. 3B, the tabular metallic base plate 109 is shaped such that the thickness gradually decreases in at least one in-plane direction (in the downward direction in FIG. 3B). The shape where the thickness gradually decrease in an in-plane direction is advantageous in manufacturing the tabular metallic base plate 109 because in metal forming, such as die casting or thixotropic casting, the material can flow easily from the thick side of the plate.

The basic thickness t1 of the tabular metallic base plate 109 can be approximately 1.5 mm, which enables metal forming relatively reliably while suppressing weight increase. A required strength can be obtained by the location of the ribs 109a. Accordingly, an appropriate balance between weight reduction and increased strength can be obtained.

The thickness in the second region R2 where the electric circuit boards 110 are disposed can be 2.0 mm or more. When the size of the tabular metallic base plate 109 is approximately 12,000 $mm^2$, an approximate thickness of 2.0 mm in the second region R2 can provide an appropriate strength without increasing the mass excessively, which leads to an appropriate balance between weight reduction and increased strength.

The thickness in the fourth region R4 where the battery 114 is disposed can be less than 1.5 mm. An approximate thickness of 1.2 mm in the fourth region R4 can provide an appropriate strength when the battery 114 is present. This thickness is feasible in the metal forming if this thickness is local. This can reduce the mass of the X-ray imaging apparatus.

The present disclosure has been described through the embodiment, which is merely an example for implementing the present disclosure and accordingly should not be construed as limiting the technical scope of the present disclosure. In other words, the present disclosure can be implemented in various other forms without departing from the technical idea and the main features of the disclosure.

According to the present disclosure, an appropriate balance between weight reduction and increased strength can be obtained for the X-ray imaging apparatus.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2021-173697 filed Oct. 25, 2021, which is hereby incorporated by reference herein in its entirety.

What is claimed is:

1. A radiographing apparatus, comprising:
    a sensor panel configured to convert incident radiation to an electric signal; and
    a tabular metallic base plate supporting the sensor panel, the tabular metallic base plate including a plurality of flat regions among which at least three flat regions are arranged in a predetermined direction, wherein the thickness of the plurality of flat regions decreases sequentially in the predetermined direction.

2. The radiographing apparatus according to claim 1, wherein the tabular metallic base plate is formed by die casting or thixomolding.

3. The radiographing apparatus according to claim 1, wherein a first flat region among the plurality of flat regions is a region where no circuit board is provided, a second flat region among the plurality of flat regions is a region where a circuit board is provided, and the second flat region is thicker than the first flat region.

4. The radiographing apparatus according to claim 1, wherein a second flat region among the plurality of flat regions is a region where a circuit board is provided, a third flat region among the plurality of flat regions is a region facing an IC chip configured to amplify the electric signal from the sensor panel, and the third flat region is thicker than the second flat region.

5. The radiographing apparatus according to claim 1, wherein a fourth flat region among the plurality of flat regions is a region with which a power supply member is in contact, a first flat region among the plurality of flat regions is a region in which the power supply member is not in contact, and the fourth flat region is thinner than the first flat region.

6. The radiographing apparatus according to claim 5, further comprising:

a housing configured to accommodate the sensor panel and the tabular metallic base plate, the housing including a holding portion for holding the power supply member, wherein the power supply member and the holding portion are in contact with the fourth flat region.

7. The radiographing apparatus according to claim 5, wherein the thickness of the fourth flat region is less than 1.5 mm.

8. The radiographing apparatus according to claim 5, wherein the fourth flat region extends to at least one end of the tabular metallic base plate.

9. The radiographing apparatus according to claim 5, wherein the power supply member is a battery.

\* \* \* \* \*